United States Patent [19]
Ettwiller et al.

[11] Patent Number: 5,962,296
[45] Date of Patent: Oct. 5, 1999

[54] **METHOD FOR CLONING AND PRODUCING *THERMOMICROBIUM ROSEUM* DNA POLYMERASE I IN *E. COLI***

[75] Inventors: Laurence Ettwiller, Beverly; Shuang-yong Xu, Lexington, both of Mass.

[73] Assignee: New England Biolabs, Inc., Beverly, Mass.

[21] Appl. No.: 09/028,361

[22] Filed: Feb. 24, 1998

[51] Int. Cl.[6] .............................. C12N 9/12; C12N 15/54
[52] U.S. Cl. .................. 435/194; 435/320.1; 435/252.3; 435/325; 435/419; 536/23.2
[58] Field of Search ................................ 435/194, 320.1, 435/252.3, 325, 419; 536/23.2

[56] References Cited

U.S. PATENT DOCUMENTS

| | | | |
|---|---|---|---|
| 4,683,195 | 7/1987 | Mullis | 435/6 |
| 4,683,202 | 7/1987 | Mullis | 435/91 |
| 4,800,159 | 1/1989 | Mullis | 435/172.3 |
| 4,889,818 | 12/1989 | Gelfand | 435/194 |
| 5,624,833 | 4/1997 | Gelfand | 435/194 |

OTHER PUBLICATIONS

Bessman, J. Biol. Chem., 233:171–177 (1957).
Buttin and Kornberg, J. Biol. Chem. 241:5419–5427 (1966).
Brutlag and Kornberg, J. Biol. Chem. 247:241–248 (1972).
Chang, J. Biol. Chem., 252:1873–1880 (1977).
Chien, J. Bacteriol., 127:1550–1557 (1976).
Lawyer, J. Biol. Chem., 264:6427–6437 (1989).
Bernad, Cell, 59:219: (1989).

*Primary Examiner*—Keith D. Hendricks
*Attorney, Agent, or Firm*—Gregory D. Williams

[57] ABSTRACT

The present invention relates to isolating DNA coding for DNA polymerase I from *Thermomicrobium roseum*, expressing the *T. roseum* DNA polymerase I gene in *E. coli* and purifying the recombinant *T. roseum* DNA polymerase I from *E. coli* cell extract.

6 Claims, 4 Drawing Sheets

FIG. 1A

```
   1 ATGCCGGAGCGCTCACGTCGACCACGCCTGGTACTCGTTGATGGACATGGGCTCGCCTAT
     M  P  E  R  S  R  R  P  R  L  V  L  V  D  G  H  G  L  A  Y    20
  61 CGCGCGTATCACGCGTTGCCCCCGAcTcTCGCGACCAGTGCCGGCGAACCGACACATGTG
     R  A  Y  H  A  L  P  P  T  L  A  T  S  A  G  E  P  T  H  V    40
 121 GTGTTCGGATTCGCCAGCATGTTATTGGAAGTGCTGAACGATTTCGAACCCGATtACGTC
     V  F  G  F  A  S  M  L  L  E  V  L  N  D  F  E  P  D  Y  V    60
 181 ATCGTCTGTTTCGATACGGGACGGAGCTTTCGACAACAACTcTACGAGGAAtACAAGGCT
     I  V  C  F  D  T  G  R  S  F  R  Q  Q  L  Y  E  E  Y  K  A    80
 241 CACCGCCCTGAAACACCGGATGACCTCAAGCACCAGCTCGAGCGAATCCGCCAACtACTC
     H  R  P  E  T  P  D  D  L  K  H  Q  L  E  R  I  R  Q  L  L   100
 301 GATGCGTTGGGAATCCCGATCGTCACGCGCGAGGGCTACGAAGCTGATGACCTCATCGGG
     D  A  L  G  I  P  I  V  T  R  E  G  Y  E  A  D  D  L  I  G   120
 361 ACACTCGCTGCTCGCGCCACTGCCAACGGGCTCGAAGTTCTGATCGTCACCGGCGATACC
     T  L  A  A  R  A  T  A  N  G  L  E  V  L  I  V  T  G  D  T   140
 421 GATTTGCTCCAGCTCGTCGATGAAGATGTCCGTGTCATCCTTCCCGGTCGCCAACGCTTC
     D  L  L  Q  L  V  D  E  D  V  R  V  I  L  P  G  R  Q  R  F   160
 481 GGCGATTACCGTGTTTATGACCGTCAAGCAGTCATCGAGCGGTACGGCTTTCCACCgGAA
     G  D  Y  R  V  Y  D  R  Q  A  V  I  E  R  Y  G  F  P  P  E   180
 541 CGGTtGCCCGGAAtACAAGGCATGgTCGgTGATCCGTCCGACAACATTCCTGGAGTCCCG
     R  L  P  G  I  Q  G  M  V  G  D  P  S  D  N  I  P  G  V  P   200
 601 GGAATCGGCGAGAAGACAGCGACACGACTCATCCAGCGATTCTCtTCCCTCGAGGAGATG
     G  I  G  E  K  T  A  T  R  L  I  Q  R  F  S  S  L  E  E  M   220
 661 CTCGACCGCATCGACGAAGTCGAACCGCCGCGACTGCGCGAGGCGCTTCGGGCGGCCCGC
     L  D  R  I  D  E  V  E  P  P  R  L  R  E  A  L  R  A  A  R   240
 721 GAAACCGTTCTCGCAAGTCGCCGCCTCGCCACCATCGTTCGCGATGCAGACATCACCCTC
     E  T  V  L  A  S  R  R  L  A  T  I  V  R  D  A  D  I  T  L   260
 781 GACCTCGAACAGGCTCGCTTCGGCGATTTCGACCGGGAACGGGTCCTCCAGCTGTTTCGC
     D  L  E  Q  A  R  F  G  D  F  D  R  E  R  V  L  Q  L  F  R   280
 841 GAACTCGAGTTCCGCAGCCTGGTTCCTCGACTTCCGCAACCGCGCCAGCCGGTGCGGAAG
     E  L  E  F  R  S  L  V  P  R  L  P  Q  P  R  Q  P  V  R  K   300
 901 ACGGCGGCACCAGCGAGTCAGCGACGCGCCGTCCTGACCGATGCCGATTTGAGCGACCTT
     T  A  A  P  A  S  Q  R  R  A  V  L  T  D  A  D  L  S  D  L   320
 961 GTCCGGGATTTGGAAACCTGTCAGGCcTTTGCGCTCGATGTAGAGACGACAGCTTTGCAT
     V  R  D  L  E  T  C  Q  A  F  A  L  D  V  E  T  T  A  L  H   340
1021 CCCATGTACgCCGACTTCGTGGGCATCGCGTTGGcGACAGcTCCCGACCGGAGTTATTAC
     P  M  Y  A  D  F  V  G  I  A  L  A  T  A  P  D  R  S  Y  Y   360
1081 GTGCCGcTCGGACACACGACGGGTGATACCCAATTCGATATCGAACAGGTGTTGCAACGA
     V  P  L  G  H  T  T  G  D  T  Q  F  D  I  E  Q  V  L  Q  R   380
1141 CTGGCGCCCTTCCTGCGCCATCCAGAGAAGCAACGTTATGCGCACCACGGCAAATACGAT
     L  A  P  F  L  R  H  P  E  K  Q  R  Y  A  H  H  G  K  Y  D   400
1201 GCCCTGGTCTTGGAACGTGCCGGTTTTCCCCGACCACACATCGACTTCGATACGATGATC
     A  L  V  L  E  R  A  G  F  P  R  P  H  I  D  F  D  T  M  I   420
1261 GCCGCCTACCTACTGGGCGAAAATGCTGTCGGCCTCAAAGAATTGGCATTCACGAAGCTC
     A  A  Y  L  L  G  E  N  A  V  G  L  K  E  L  A  F  T  K  L   440
1321 GGGTGGGAGATGGAGGAAATCACCGAGCTAATTGGACGGGGCAAGAAGCAACTCACGATG
     G  W  E  M  E  E  I  T  E  L  I  G  R  G  K  K  Q  L  T  M   460
1381 GATCGCGCCGAGATCGCACGGGTCACGCAATACGCCTGTGCCGACGTCGAGGCGACATAC
     D  R  A  E  I  A  R  V  T  Q  Y  A  C  A  D  V  E  A  T  Y   480
1441 CGGTTAGTcGAGGTACTTcGTCCACAATTcGAAGCCCACAATCAAcTCCGGCTGTTCACC
     R  L  V  E  V  L  R  P  Q  F  E  A  H  N  Q  L  R  L  F  T   500
1501 GAAATCGAACTTCTTTTTCATCGATGTACTGATCGACATGGAAAAGGCGGGATTCGCGATC
     E  I  E  L  L  F  I  D  V  L  I  D  M  E  K  A  G  F  A  I   520
```

FIG. 1B

```
1561  GATGTGCCGTACCTCGAACAGCTcTCCATCATGCTGGACGGTCAGCTGCATGCGCTCGAG
       D   V   P   Y   L   E   Q   L   S   I   M   L   D   G   Q   L   H   A   L   E         540
1621  CGACGCATcTACGAACTGGCTGGGCATCCCTTCAACATCACTTCGCCACAACAGTTGAGC
       R   R   I   Y   E   L   A   G   H   P   F   N   I   T   S   P   Q   Q   L   S         560
1681  ACCCTGCTTTTCGACGAACTCGGCCTGCCTCGCGGCAAACGAACCAAGACTGGGTATTCA
       T   L   L   F   D   E   L   G   L   P   R   G   K   R   T   K   T   G   Y   S         580
1741  GTTTCTCAAGAAGTGCTCGAGAATCTCCGCGATACCCACCCCATCGTCGAGGCGATTTTG
       V   S   Q   E   V   L   E   N   L   R   D   T   H   P   I   V   E   A   I   L         600
1801  GAATACCGGCAACTCCTCAAATTGAAGTCGACGTACGTCGATGCCTTACCGCGGCAAGTC
       E   Y   R   Q   L   L   K   L   K   S   T   Y   V   D   A   L   P   R   Q   V         620
1861  CAtCCCCAAACCGGACGCGTCCACACGATTTTCCATCAAACTGTCGCGGCCACCGGCCGC
       H   P   Q   T   G   R   V   H   T   I   F   H   Q   T   V   A   A   T   G   R         640
1921  TTGAGTTCCTCCGACCCGAACCTTCAGAACATTCCTGCTCGCGGCGAGCTGGGACTCGCC
       L   S   S   S   D   P   N   L   Q   N   I   P   A   R   G   E   L   G   L   A         660
1981  GTTCGCCGCGCCTTCATCGCTGACAATCGCCCAGGTTATCGAATCGCCGATGAACCGATC
       V   R   R   A   F   I   A   D   N   R   P   G   Y   R   I   A   D   E   P   I         680
2041  CTGCTTCTTTCAGCTGACTACTCGCAGATCGAGCTTCGCCTGATGGCTCACTTCAGTCAG
       L   L   L   S   A   D   Y   S   Q   I   E   L   R   L   M   A   H   F   S   Q         700
2101  GATCCCGCACTCCTGCGTGCCTTCGCTGAAGGCAAGGACATTCACGCGGCTACCGCGTCT
       D   P   A   L   L   R   A   F   A   E   G   K   D   I   H   A   A   T   A   S         720
2161  GAAGTGTTCGGGGTCCCACTCGACGCGGTCACGCCAGAGATGCGTCGCATCGCGAAAGTC
       E   V   F   G   V   P   L   D   A   V   T   P   E   M   R   R   I   A   K   V         740
2221  GTCAATTTCGGCATCATGTATGGGATGCAAGCGTACGGCCTCGCTCGCGACACCGGTATG
       V   N   F   G   I   M   Y   G   M   Q   A   Y   G   L   A   R   D   T   G   M         460
2281  AGCCGTCAAGACGcACAGCGCTTCATCGAAGCGTATTTTCAGCGCTTCCCCGGCGTCGCC
       S   R   Q   D   A   Q   R   F   I   E   A   Y   F   Q   R   F   P   G   V   A         480
2341  CGTTATCTCGAAGAAACGAGACGCCGTGCGGCCGAACTCGGTTACGTCGAAACGCTCTTC
       R   Y   L   E   E   T   R   R   R   A   A   E   L   G   Y   V   E   T   L   F         500
2401  GGCCGGCGGCGATACTTGCCCGAAATCACCTCCTCCAACCCGGCACGAcGGCAGGCGGCC
       G   R   R   R   Y   L   P   E   I   T   S   S   N   P   A   R   R   Q   A   A         520
2461  GAACGGATGGCGGTCAATATGCCGCTGCAAGGCACCGCAGCCGATATTATGAAGTTGGTC
       E   R   M   A   V   N   M   P   L   Q   G   T   A   A   D   I   M   K   L   V         540
2521  ATGATCGCTGTCCACCGACCGCTGGGCGAACGCGGCTTGCGCAGCCGCATGCTGCTCCAG
       M   I   A   V   H   R   P   L   G   E   R   G   L   R   S   R   M   L   L   Q         560
2581  GTTCATGACGAACTCGTCTTGGAGGTACCGGAGTCGGAACTTGCGACGACAACGGAACTC
       V   H   D   E   L   V   L   E   V   P   E   S   E   L   A   T   T   T   E   L         580
2641  GTCACGACACGCATGAGTCGCGTCGTCGAACCCAGCGTGCCACTCGAAGTCGATGCCAAA
       V   T   T   R   M   S   R   V   V   E   P   S   V   P   L   E   V   D   A   K         600
2701  GCGGGGCCCAATTGGGCTGACCTTGAGCCGGTTCGAGTGAAACTCTCCCACTAG
       A   G   P   N   W   A   D   L   E   P   V   R   V   K   L   S   H   *       918
```

METHOD FOR CLONING AND PRODUCING *THERMOMICROBIUM ROSEUM* DNA POLYMERASE I IN *E. COLI*

BACKGROUND OF THE INVENTION

DNA polymerases are a family of enzymes involved in DNA repair and replication. Extensive research has been conducted on the isolation of DNA polymerases from mesophilic microorganisms such as *E. coli* (Bessman, et al., *J. Biol. Chem.* 233:171–177 (1957); Buttin and Kornberg *J. Biol. Chem.* 241:5419–5427 (1966)).

Examples of DNA polymerases isolated from *E. coli* include *E. coli* DNA polymerase I and T4 DNA polymerase. These enzymes have a variety of uses in recombinant DNA technology including DNA labeling by nick translation, second-strand cDNA synthesis in cDNA cloning, and DNA sequencing (Maniatis et al., *Molecular Cloning: A Laboratory Manual* (1982).

U.S. Pat. Nos. 4,683,195, 4,683,202 and 4,800,159 disclosed the use of the above enzymes in a process for amplifying, detecting, and/or cloning nucleic acid sequences. This process, commonly referred to as polymerase chain reaction (PCR), involves the use of a polymerase, primers and nucleotide triphosphates in amplifying existing nucleic acid sequences.

Some of the DNA polymerases discussed above possess a 3'–5' exonuclease activity which provides a proofreading function that gives DNA replication much higher fidelity than it would have if synthesis were the result of only a one base-pairing selection step (Brutlag, D. and Kornberg, A., *J. Biol Chem.*, 247:241–248 (1972)). DNA polymerases with 3'–5' proofreading exonuclease activity have a substantially lower base incorporation error rate when compared with a non-proofreading exonuclease-possessing polymerase (Chang, L. M. S., *J. Biol. Chem.* 252:1873–1880 (1977)).

Research has also been conducted on the isolation and purification of DNA polymerases from thermophiles, such as *Thermus aquaticus*. Chien, A. et al. *J. Bacteriol.* (1976) 127:1550–1557, discloses the isolation and purification of a DNA polymerase with a temperature optimum of 80° C. from *T. aquaticus* YT1 strain. The Chien et al., purification procedure involves a four-step process. These steps involves preparation of crude extract, DEAE-Sephadex chromatography, phosphocellulose chromatography and chromatography on DNA cellulose.

US Pat. No. 4,889,818 discloses a purified thermostable DNA polymerase from *T. aquaticus*, Taq polymerase, having a molecular weight of about 86,000 to 90,000 daltons prepared by a process substantially identical to the process of Kaledin with the addition of the substitution of a phosphocellulose chromatography step in lieu of chromatography on single-strand DNA-cellulose. In addition, European Patent Application 0 258 017 disclose Taq polymerase as the preferred enzyme for use in the PCR process discussed above. Research has indicated that while Taq DNA polymerase has a 5'–3' polymerase-dependent exonuclease function, Taq DNA polymerase does not possess a 3'–5' proofreading exonuclease function (Lawyer, et al. *J. Biol. Chem.* 264:11, p. 6427–6437 (1989). Bernard, et al. *Cell* 59:219 (1989). As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the replication cycle that error occurs (e.g., in an early replication cycle), the entire DNA amplified could contain the erroneously incorporated base, thus, giving rise to a mutated gene product.

Accordingly, there is a continuing need in the art to obtain and produce a purified, thermostable DNA polymerase with 3'–5' proofreading exonuclease activity that may be used to improve the DNA polymerase processes described above. One such enzyme (describe in more detail below), DNA polymerase I from *Thermomicrobium roseum*, a Gram negative, pleomorphic, and thermophilic bacterium, has been cloned and expressed in *E. coli*.

SUMMARY OF THE INVENTION

In accordance with the present invention, there is provided a novel as well as Pol I like DNA polymerase from *T. roseum* as well as the DNA sequence which encodes that polymerase. DNA polymerase has an apparent molecular weight of approximately 103,000 daltons and an half life of 15 minutes at 95° C.

More specifically, in accordance with the present invention, it has been discovered that DNA coding for Pol I related DNA polymerases from Eubacteria species share conserved regions with substantial homology both at the DNA and amino acid level. Thus, in accordance with the present invention, degenerated primers can be synthesized from the conserved regions and used to amplify a DNA fragment coding for a portion of DNA polymerase I from *T. roseum*. The upstream and downstream DNA sequences coding for the DNA polymerase were obtained by direct sequencing of the inverse PCR products or by sequencing the cloned PCR product. Once the DNA coding for the entire DNA polymerase has been isolated, it can be used to construct expression clone in order to produce large amounts of the DNA polymerase. *T. roseum* DNA polymerase I possesses 3'–5' proofreading exonuclease activity. This is the first instance of a proofreading thermostable DNA polymerase I (Pol I like DNA polymerase) isolated from Eubacteria.

BRIEF DESCRIPTION OF THE DRAWINGS

FIG. 1 shows the Nucleotide sequence and the predicted amino acid sequences (SEQ ID NO:1) of the *T. roseum* DNA polymerase I.

DETAILED DESCRIPTION OF THE INVENTION

A recombinant Pol I like DNA polymerase is cloned from *T. roseum*, a thermophilic microorganism found in the hot spring in Yellowstone National Park, Wyo. USA. This strain is available from the American Type Culture Collection (ATCC No. 27502). The organism is a Gram⁻ pleomorphic rod bacterium with a temperature growth optimum at about 70° C.

The method described herein by which the *T. roseum* DNA polymerase I gene is cloned and expressed includes the following steps:

1. The genomic DNA is purified from *T. roseum* cells.

2. Conserved regions in Pol I DNA polymerase are found by nucleotide sequence comparison of Pol I type DNA polymerases from Eubacteria. Based on conserved sequences, one set of degenerate primers is designed and an initial PCR is carried out using the degenerate primers to amplify part of the *T. roseum* DNA polymerase I (670 bp).

3. Inverse PCR is used to amplify and sequence the upstream and downstream sequences. *T. roseum* genomic DNA is digested with restriction enzymes that will give rise to reasonable size template DNA for inverse PCR reaction. The digested DNA is self-ligated at a low DNA concentration (less than 2 microgram per ml). The ligated circular DNA is used as templates for inverse PCR reaction using a set of primers that annealed to the end of the initial fragment. The inverse PCR product is cloned in pUC19 and sequenced. Alternatively, the inverse PCR products are purified in low-melting agarose gel and sequenced directly using primers. The newly derived DNA sequences are compared with sequences in Genbank using Blast program. This step is repeated until the start codon was found upstream and stop codon was found downstream. The entire *T. roseum* DNA polymerase gene is amplified in PCR and re-sequenced with primers to ensure 100% accuracy of the sequence.

4. The *T. roseum* DNA polymerase I gene is amplified by PCR using Vent® DNA polymerase and then cloned into a pET21a vector. *T. roseum* DNA polymerase I production is induced by addition of IPTG in cell culture.

5. *T. roseum* DNA polymerase I is purified by heat-denaturation of *E. coli* proteins at 70° C. for 30 min. The *T. roseum* DNA polymerase I is further purified by chromatography through DEAE and heparin Sepharose® columns.

6. The purified *T. roseum* DNA polymerase I is used in polymerization assay at 70° C., in thermostability test at 95° C., in exonuclease assay at 70° C., and in PCR reactions at 60° C. to 94° C.

7. The purified *T. roseum* DNA polymerase I is subjected to N-terminal amino acid sequencing to confirm the correct start of translation in *E. coli*.

The following Examples are given to illustrate embodiments of the present invention as it is presently preferred to practice. It will be understood that these Examples are illustrative, and that the invention is not to be considered as restricted thereto as indicated in the appended claims.

All references cited above and below are herein incorporated by reference.

EXAMPLE I

1. Cloning of *T. roseum* DNA Polymerase I Gene

*T. roseum* DNA polymerase I gene was cloned by PCR and inverse PCR without library construction. Two conserved and closely spaced regions of Pol I polymerases were found and degenerate primers based on the conserved region were synthesized:

5' TCCGA(CT)CCCAACCT(GC)CAGAACATCCC 3' (138-151) (SEQ ID NO:2)

5' AGGA(GC)(GC)AGCTCGTCGTG(GC)ACCTG 3' (138-152) (SEQ ID NO:3).

PCR was performed using 50 ng of *T. roseum* genomic DNA, 0.5 mM of primers, 0.25 mM dNTP and 2 mM MgCl₂ in 1×Taq buffer (10 mM Tris-HCl, pH 9, 50 mM KCl and 0.1% Triton® X-100). PCR conditions were 40 cycles at 95° C. 1 min, 50° C., 1 min, 72° C., 1 min. The unique product of the predicted length of 650–700 bp was cloned and sequenced. This DNA sequence is 670 bp and shows 55.7% and 56% identity to *E. coli* and Taq DNA polymerase I genes, respectively. Two sets of inverse PCR primers were made based on the 670 bp sequence.

To amplify the downstream sequence, first round of inverse PCR primers used were:
5' CGAACGCGGCTTGCGCAGCCGCAT 3' (142-79) (SEQ ID NO:4)
5' TGGACAGCGATCATGGCCAACTTC 3' (142-80). (SEQ ID NO:5)

A second round of inverse PCR primers to amplify the downstream sequence were:
5' ATTGGGCTGACCTTGAGCCGG 3' (163-108) (SEQ ID NO:6)
5' CCCGCTTTGGCATCGACTTCG 3' (163-107) (SEQ ID NO:7)

To amplify the upstream sequence of the known 670 bp sequence, first round of inverse PCR primers used were:
5' GACTACTCGCAGATCGAGCTTCGC 3' (160-183) (SEQ ID NO:8)
5' GCGATTGCTAGCGATGAAGGCGCGG 3' (160-184). (SEQ ID NO:9)

Second round of inverse PCR primers were:
5' GACATGGAAAAGGCGGGATTCGCGATC 3' (161-132) (SEQ ID NO:10)
5' TCGATTTCGGTGAACAGCCGGA 3' (161-133).(SEQ ID NO:11)

Third round of inverse PCR primers were:
5' GATGCAAAGCTGTCGTCTCTACATC 3' (163-06) (SEQ ID NO:12)
5' TGTACCCCGACTTCGTGGGCATCG 3' (163-07).(SEQ ID NO:13)

Forth round of inverse PCR primers were:
5' TCCCGGGAATCGGCGAGAAGAC 3' (168-115) (SEQ ID NO:14)
5' CCAGGAATGTTGTCGGACGG 3' (168-114).(SEQ ID NO:15)

The genomic DNA used in inverse PCR was digested with the appropriate restriction enzyme and self-ligated. 2 µg of genomic DNA was digested in a total volume of 200 µl using 20 units of restriction enzymes. After phenol extraction and ethanol precipitation, the DNA was ligated overnight at 16° C. in a total volume of 500 µl to facilitate intramolecular ligation. Inverse PCR conditions were: 50 ng of circularized genomic DNA, 95° C. 1 min, 55° C. 1 min, 72° C. 1 to 2 min, 0.5 mM of primers, 0.25 mM dNTP and 2 mM MgCl₂, 5 units of Taq DNA polymerase in 1×Taq Buffer.

Amplified products were found in HaeII, AvaI, BsaHI and EcoO109I digested and self-ligated DNA for the first inverse PCR amplification of the upstream of the initial 670 bp fragment. In second round of inverse PCR, amplified product was found in PvuII digested and ligated DNA. In third round of inverse PCR, inverse PCR products were found in the AvaI and HaeII digested and ligated DNA. In the fourth round of inverse PCR, inverse PCR products were found in the RsaI and NlaIII digested and self-ligated genomic DNA.

In the first round of inverse PCR to amplify the downstream sequence, inverse PCR products were found in PvuI, SphI, SacI and SacII digested and self-ligated DNA.

Inverse PCR products were cloned in pUC19 and the insert was sequenced. Alternatively, the inverse PCR products were gel-purified in low-melting agarose gel and sequenced directly without the cloning step. The newly-derived sequence was analyzed by Blast and FASTA program to confirm that they are homologous to known Pol I polymerase genes. The entire *T. roseum* polymerase gene was found to be 2754 bp, encoding a protein of 917 amino acid residues with a predicted molecular weight of 103.6 kDa.

2. Expression of *T. roseum* DNA Polymerase I in *E. coli*

The entire polymerase gene was amplified by PCR using two primers. The forward primer contains an NdeI site and the reverse primer contains an EcoRI site after the stop codon.

5' GGGGAATTCCATATGCCGGAGCGCT-CACGTCGACCACG 3' (175-49) (SEQ ID NO:16)
5' GCCGGAATTCCTAGTGG-GAGAGATTTCACTCGAACCG G 3' (175-55) (SEQ ID NO:17).

PCR conditions were 95° C. 1 min, 55° C. 1 min, 72° C. 2 min, for 20 cycles. *T. roseum* polymerase gene was digested with NdeI and EcoRI and cloned into T7 expression vector pET21a (Novagen). The ligated DNA was used to transform *E. coli* cells ER2566 and transformants were plated on Amp plates. In plasmid mini-prep screening, one out of four was found to contain the correct size insert. *E. coli* cells carrying the insert plasmid were induced by addition of IPTG for 3 h at 37° C. Cell lysates were prepared as follows.

Cells were lysed by sonication. The clarified lysate was then treated at 70° C. for 10–30 min to inactivate the endogenous polymerases. 20 μg of DNaseI treated calf thymus DNA was mix with 25 mM of each dNTP, 1 mM MgCl$_2$, [H$^3$] dTTP (1 μCi) together with a fraction of the crude extract in a total volume of 50 μl. After 15 min at 70° C., the reaction was stopped by addition of SDS (1%) and EDTA (50 mM) and total mixture was spotted onto a disc. The disc was washed twice in a 10% TCA solution and then washed in isopropanol. The disc was then dried and counted in a scintillation counting machine.

3. Purification of the Recombinant *T. roseum* DNA Polymerase

Five ml of an overnight culture was inoculated into 1 liter of LB+Amp (100 μg/ml). After incubation at 37° C. until OD$_{600}$=0.5, IPTG was added to 2 mM final concentration to induce the *T. roseum* DNA polymerase I production. After IPTG induction for 3 hours at 37° C., cells were harvested by centrifugation at 4000 rpm for 30 min. Cell pellets were resuspended in 24 ml lysis buffer (20 mM Tris-HCl, pH 8, 500 mM NaCl, 0.1 mM EDTA, 0.1% Triton X-100). Cells were lysed by sonication. Cell debris were removed by centrifugation at 10,000 rpm for 30 min. The clarified lysate was treated at 70° C. for 30 min. Heat denatured proteins were removed by centrifugation at 10,000 rpm for 30 minutes. The solution was then dialyzed against 20 mM Bistris pH 6 and 75 mM NaCl. The proteins were loaded onto a DEAE column equilibrated with 20 mM Bistris pH 6, 75 mM NaCl. *T. roseum* polymerase I was eluted at the NaCl concentration of 200 mM (in 20 mM Bistris). Fractions containing the polymerase activity were dialyzed against 0.1 M Tris-HCl, pH 8 and loaded onto a heparin Sepharose® column equilibrated with 0.1 M Tris-HCl, pH 8. Elution of *T. roseum* polymerase I occurred at approximately 0.4 M NaCl, o.1 M Tris-HCl.

The purified *T. roseum* DNA polymerase I was subjected to electrophoresis in 4%–20% SDS-PAGE gradient gel. Two protein bands were detected. The major protein band corresponds to the predicted molecular mass of the *T. roseum* polymerase I at about 103 kDa. N-terminal amino acid sequence analysis of the 103 kDa protein confirmed that it is the *T. roseum* polymerase I protein.

4. 3'–5' Exonuclease Activity Assay

Figure 2:
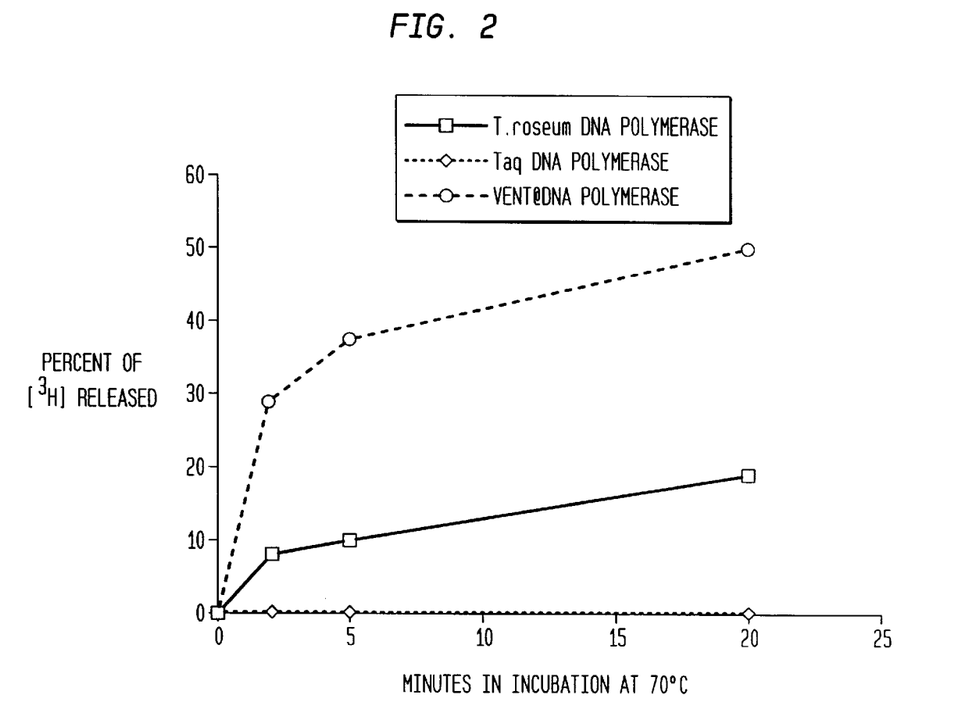
FIG. 2 illustrates the 3'–5' exonuclease activity assay for Vent®, *T. roseum* and Taq DNA polymerases in percent of [$^3$H] released as the function of time.

The predicted amino acid sequence of *T. roseum* polymerase I contains all the conserved amino acid residues in the 3'–5' exonuclease domain (exoI, II and III). Table I shows the conserved amino acids of *T. roseum* polymerase I and the *E. coli* DNA polymerase I in the 3'–5' exonuclease domain. A 3'–5' exonuclease activity assay was performed using the purified *T. roseum* polymerase I. *T. roseum* DNA polymerase or polymerases with a well characterized exonuclease functions (Vent® DNA polymerase) were incubated with 1 μg of EcoRI digested and [$^3$H]-thymidine labeled double-stranded DNA (0.8×10$^5$ CPM/μg) in Vent® polymerase buffer. After incubation period of 20 minutes, the exonuclease digested DNA was assayed by measuring the acid-soluble [$^3$H] label (shown in FIG. 2).

TABLE 1

Conserved amino acid residues in 3'–5' exonuclease domain in *E. coli* and Tro polymerase I

|  | Exo I | Exo II | Exo III |
|---|---|---|---|
| *E. coli* Pol I | D$_{355}$TE$_{357}$ | NLKY$_{423}$D$_{424}$ | Y$_{497}$AAED$_{501}$ |
| Tro Pol I | D$_{333}$VE$_{335}$ | HGKY$_{399}$D$_{400}$ | Y$_{471}$ACAD$_{475}$ |

5. Thermostability of *T. roseum* Polymerase I

Figure 3:
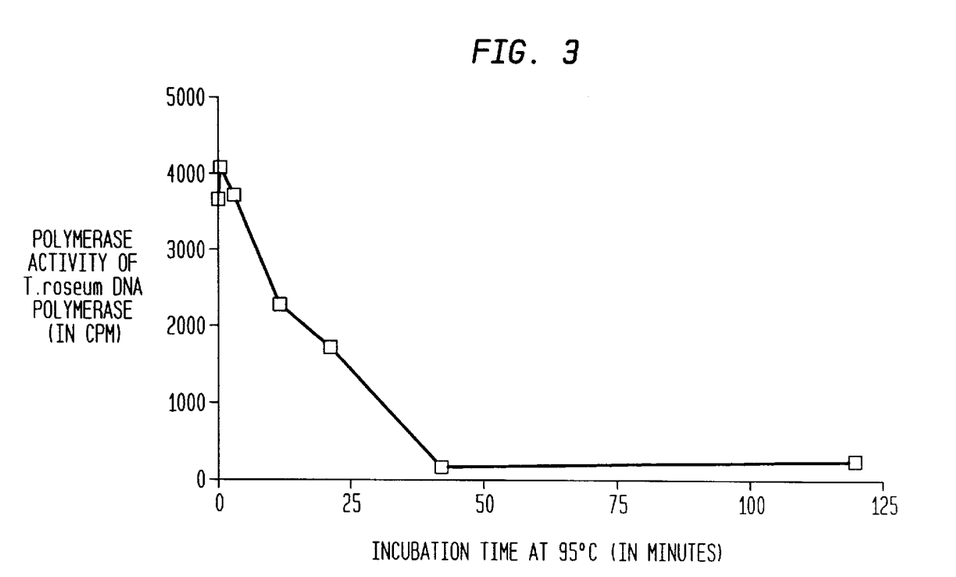
FIG. 3 illustrates the thermostability of the recombinant *T. roseum* DNA polymerase I at 95° C. The polymerase reaction assay was carried out at 70° C. for 10 min after incubation of the DNA polymerase at 95° C. for a various time.

The thermostability of the recombinant *T. roseum* DNA polymerase was determined by the following method. Purified *T. roseum* DNA polymerase was preincubated at 95° C. in a buffer containing 0.1 M Tris-HCl, 0.2 M NaCl in 50% glycerol. At time 0.5; 2.5; 5; 10; 20; 40, and 120 min, tubes containing the enzymes were removed from 95° C. and polymerase activity was measured by determining incorporation of deoxynucleotide [$^3$H] TTP into DNA. The half-life of *T. roseum* polymerase I at 95° C. was about 15 minutes (shown in FIG. 3).

EXAMPLE 2

1. Purification of the Native DNA Polymerase I from *T. roseum*

*T. roseum* cells were cultured in ATCC medium 655 for 48 hours at 70° C. A total of about 10 grams of cells were resuspended in a sonication buffer (50 mM Tris-HCl, pH 8, 10 mM β-mercaptoethanol). Cells were lysed by sonication for a total of 10 min at 4° C. Cell debris was removed by centrifugation. Cleared cell lysate was transferred to a new tube and protease inhibitor cocktail tablets were added to prevent protease cleavage of DNA polymerase I. The cell extract was loaded onto a 40 ml DEAE-Sepharose® column. Proteins were eluted with 50 mM Tris-HCl, 2 mM β-mercaptoethanol, 10% glycerol, NaCl gradient of 0–0.3 M. Two ml fractions were collected and each fraction was assayed for DNA polymerase activity. The polymerase activity assay consisted of 20 μg of activated calf-thymus DNA, 33 μM dNTP, 50 mM Tris-HCl, 1 μCi [³H]TTP, 2 mM MgCl₂, 10 μl of each protein fraction in a total volume of 100 μl. The assayed was carried out at 70° C. for 15 min. Fractions 47 to 63 contain thermostable DNA polymerase activity and these fractions were pooled and dialyzed in a buffer containing 50 mM Tris-HCl, 2 mM β-mercaptoethanol, 10% glycerol at 4° C.

The dialyzed proteins were loaded onto a 40 ml heparin-Sepharose® column. The column was washed with 50 ml of 50 mM Tris-HCl, 2 mM β-mercaptoethanol, 10% glycerol. Proteins were eluted with 100 ml of 0–0.5M NaCl gradient in 50 mM Tris-HCl, 2 mM β-mercaptoethanol, 10% glycerol. Two ml fractions were collected and each fraction was assayed for DNA polymerase I activity. It was found that fractions 52–58 contain DNA polymerase activity. The total yield was about 1400 units of DNA polymerase. The purified DNA polymerase was dialyzed in 2 liters of 50 mM Tris-HCl, 2 mM β-mercaptoethanol, 10% glycerol overnight at 4° C.

2. Thermostability of *T. roseum* DNA Polymerase I

The purified *T. roseum* DNA polymerase I was incubated at 75° C., 80° C., 85° C. for 30 min and then assayed for DNA polymerase activity. It was found that *T. roseum* DNA polymerase I is stable at 70° C. to 85° C. and it displayed 70 to 100% activity at this temperature range.

3. The use of *T. roseum* DNA Polymerase I in PCR

The purified *T. roseum* DNA polymerase I was used in PCR reaction to amplify the BsoBI restriction endonuclease gene from *Bacillus stearothermophilus* genomic DNA. The two PCR primer sequence are:

5'  AAGCTTGCATGCGGAGGTTTAATAAT-GAACACTCAAAAACCTTT TGAA 3' (136-164) (SEQ ID NO:18)
5'  CTAGGATCCTTATATATTAATTATC-CATCTACAAAGAGA 3' (136-165) (SEQ ID NO:19)

PCR conditions were 95° C. 30 sec, 55° C. 1 min, 72° C. 1 min for 20 cycles. A 972 bp DNA fragment was clearly detected after PCR amplification from the genomic DNA. It was concluded that *T. roseum* DNA polymerase I is relatively thermostable and can be used in PCR reaction.

What is claimed is:

1. A substantially pure thermostable DNA polymerase endogenous to *Thermomicrobium roseum*, ATCC No. 27502, wherein said polymerase has a molecular weight of about 103,000 daltons.

2. An isolated DNA which encodes a thermostable DNA polymerase with 3'–5' exonuclease activity from *Thermomicrobium roseum* ATCC No. 27502.

3. A cloning vector comprising the isolated DNA of claim 2.

4. A host cell transformed with the cloning vector of claim 3.

5. The polymerase of claim 2, wherein said polymerase is isolated from a recombinant organism transformed with the vector of claim 3.

6. A method of producing a *Thermomicrobium roseum* comprising culturing a host cell transformed with the vector of claim 3 under conditions suitable for expression of said endonuclease.

* * * * *

UNITED STATES PATENT AND TRADEMARK OFFICE
CERTIFICATE OF CORRECTION

PATENT NO. : 5,962,296
DATED : October 5, 1999
INVENTOR(S) : Laurence Ettwiller, et al.

It is certified that error appears in the above-identified patent and that said Letters Patent is hereby corrected as shown below:

Column 1, line 18    replace "(1982)" with --(1982))--

Column 1, line 43    replace "involves" with --involve--

Column 1, line 54    replace "disclose" with --discloses--

Column 1, line 60    replace "(1989)" with --(1989))--

Column 2, line 16    replace "an" with --a--

Column 4, line 58    delete "of the" first occurrence

Column 5, line 36    replace "mix" with --mixed--

Column 6, line 15    replace "exol" with --ExoI--

Column 6, lines 20-21    replace "functions" with --function--

Column 7, line 3    replace "assayed" with --assay--

UNITED STATES PATENT AND TRADEMARK OFFICE
CERTIFICATE OF CORRECTION

PATENT NO. : 5,962,296
DATED : October 5, 1999
INVENTOR(S) : Laurence Ettwiller, et al.

It is certified that error appears in the above-identified patent and that said Letters Patent is hereby corrected as shown below:

Column 5, line 21    replace "GAGAGATTTCACTCGAACCGG" with --GAGAGTTTCACTCGAACCGG -

Signed and Sealed this

Eighteenth Day of April, 2000

Attest:

Q. TODD DICKINSON

Attesting Officer    *Director of Patents and Trademarks*

UNITED STATES PATENT AND TRADEMARK OFFICE
CERTIFICATE OF CORRECTION

PATENT NO. : 5,962,296
DATED : October 5, 1999
INVENTOR(S) : Laurence Ettwiller and Shuang-yong Xu It is certified that error appears in the above-identified patent and that said Letters Patent is hereby corrected as shown below:

Sheet 3 of 4, in the legend, replace "Vent@" with --Vent®--

Figure 4:
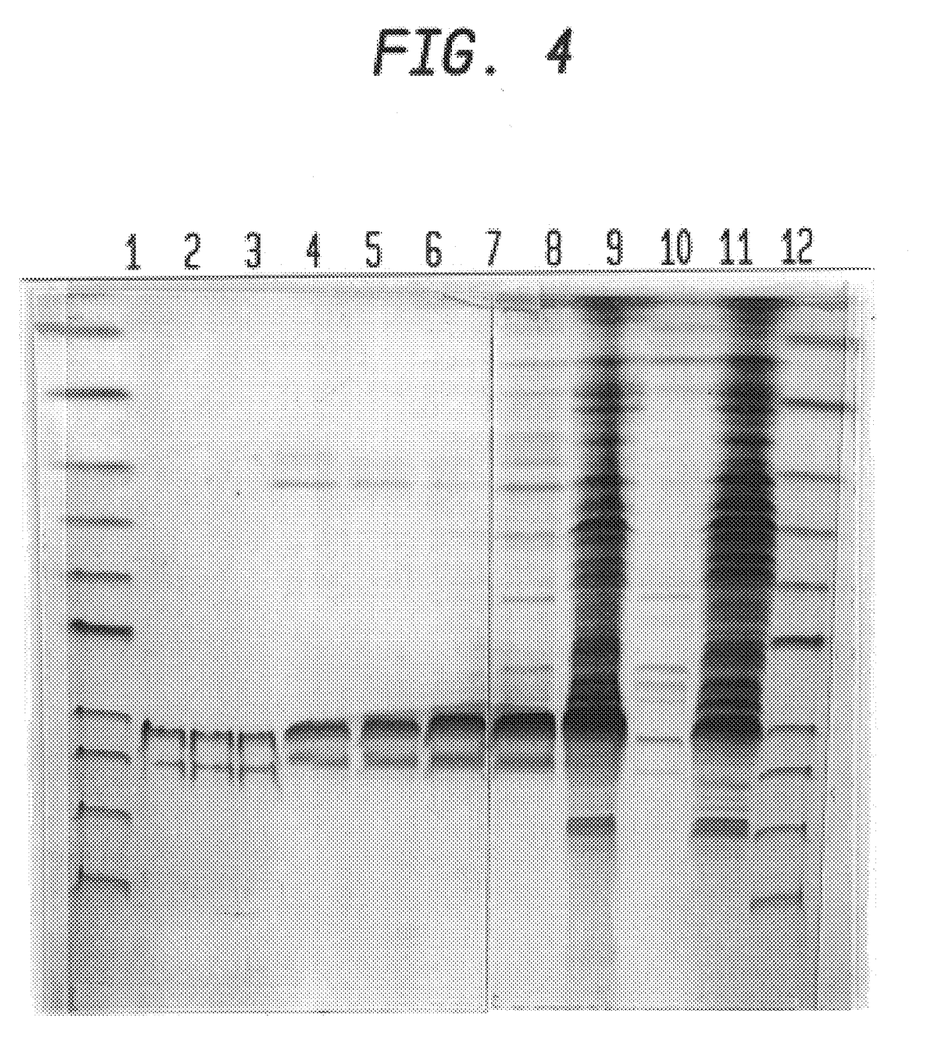
FIG. 4 illustrates the SDS-PAGE gel showing the purification steps for recombinant *T. roseum* DNA polymerase. Lane 1 and 12, protein size marker; lane 2, cell extract of non-induced cells; lane 3, cell extract of non-induced cells after heat denaturation at 70° C. for 30 min; lane 4, cell extract of IPTG-induced cells; lane 5, cell extract of IPTG-induced cells after heat denaturation at 70° C. for 30 min. lanes 6 to 8, fractions from DEAE column; lanes 9–11, fractions from heparin Sepharose® column. The purified recombinant *T. roseum* DNA polymerase appears to have two different migration patterns on SDS-PAGE gel. One migrates at about 103,000 daltons, the other migrates at about 120,000 daltons.

Sheet 4 of 4, replace "Fig. 4" with substitute "Fig. 4"

Signed and Sealed this

First Day of August, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 2754 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...2751
        (D) OTHER INFORMATION:

(xi) SEQUENCE DESCRIPTION: SEQ ID NO:1:

```
ATG CCG GAG CGC TCA CGT CGA CCA CGC CTG GTA CTC GTT GAT GGA CAT        48
Met Pro Glu Arg Ser Arg Arg Pro Arg Leu Val Leu Val Asp Gly His
1               5                   10                  15

GGG CTC GCC TAT CGC GCG TAT CAC GCG TTG CCC CCG ACT CTC GCG ACC        96
Gly Leu Ala Tyr Arg Ala Tyr His Ala Leu Pro Pro Thr Leu Ala Thr
                20                  25                  30

AGT GCC GGC GAA CCG ACA CAT GTG GTG TTC GGA TTC GCC AGC ATG TTA       144
Ser Ala Gly Glu Pro Thr His Val Val Phe Gly Phe Ala Ser Met Leu
            35                  40                  45

TTG GAA GTG CTG AAC GAT TTC GAA CCC GAT TAC GTC ATC GTC TGT TTC       192
Leu Glu Val Leu Asn Asp Phe Glu Pro Asp Tyr Val Ile Val Cys Phe
        50                  55                  60

GAT ACG GGA CGG AGC TTT CGA CAA CAA CTC TAC GAG GAA TAC AAG GCT       240
Asp Thr Gly Arg Ser Phe Arg Gln Gln Leu Tyr Glu Glu Tyr Lys Ala
65                  70                  75                  80

CAC CGC CCT GAA ACA CCG GAT GAC CTC AAG CAC CAG CTC GAG CGA ATC       288
His Arg Pro Glu Thr Pro Asp Asp Leu Lys His Gln Leu Glu Arg Ile
                85                  90                  95
```

-continued

| | |
|---|---|
| CGC CAA CTA CTC GAT GCG TTG GGA ATC CCG ATC GTC ACG CGC GAG GGC<br>Arg Gln Leu Leu Asp Ala Leu Gly Ile Pro Ile Val Thr Arg Glu Gly<br>100                       105                     110 | 336 |
| TAC GAA GCT GAT GAC CTC ATC GGG ACA CTC GCT GCT CGC GCC ACT GCC<br>Tyr Glu Ala Asp Asp Leu Ile Gly Thr Leu Ala Ala Arg Ala Thr Ala<br>115                     120                    125 | 384 |
| AAC GGG CTC GAA GTT CTG ATC GTC ACC GGC GAT ACC GAT TTG CTC CAG<br>Asn Gly Leu Glu Val Leu Ile Val Thr Gly Asp Thr Asp Leu Leu Gln<br>130                     135                   140 | 432 |
| CTC GTC GAT GAA GAT GTC CGT GTC ATC CTT CCC GGT CGC CAA CGC TTC<br>Leu Val Asp Glu Asp Val Arg Val Ile Leu Pro Gly Arg Gln Arg Phe<br>145                     150                   155            160 | 480 |
| GGC GAT TAC CGT GTT TAT GAC CGT CAA GCA GTC ATC GAG CGG TAC GGC<br>Gly Asp Tyr Arg Val Tyr Asp Arg Gln Ala Val Ile Glu Arg Tyr Gly<br>                165                   170                   175 | 528 |
| TTT CCA CCG GAA CGG TTG CCC GGA ATA CAA GGC ATG GTC GGT GAT CCG<br>Phe Pro Pro Glu Arg Leu Pro Gly Ile Gln Gly Met Val Gly Asp Pro<br>                    180                   185                  190 | 576 |
| TCC GAC AAC ATT CCT GGA GTC CCG GGA ATC GGC GAG AAG ACA GCG ACA<br>Ser Asp Asn Ile Pro Gly Val Pro Gly Ile Gly Glu Lys Thr Ala Thr<br>                195                   200                   205 | 624 |
| CGA CTC ATC CAG CGA TTC TCT TCC CTC GAG GAG ATG CTC GAC CGC ATC<br>Arg Leu Ile Gln Arg Phe Ser Ser Leu Glu Glu Met Leu Asp Arg Ile<br>210                     215                    220 | 672 |
| GAC GAA GTC GAA CCG CCG CGA CTG CGC GAG GCG CTT CGG GCG GCC CGC<br>Asp Glu Val Glu Pro Pro Arg Leu Arg Glu Ala Leu Arg Ala Ala Arg<br>225                     230                   235            240 | 720 |
| GAA ACC GTT CTC GCA AGT CGC CGC CTC GCC ACC ATC GTT CGC GAT GCA<br>Glu Thr Val Leu Ala Ser Arg Arg Leu Ala Thr Ile Val Arg Asp Ala<br>                    245                   250                  255 | 768 |
| GAC ATC ACC CTC GAC CTC GAA CAG GCT CGC TTC GGC GAT TTC GAC CGG<br>Asp Ile Thr Leu Asp Leu Glu Gln Ala Arg Phe Gly Asp Phe Asp Arg<br>                    260                   265                  270 | 816 |
| GAA CGG GTC CTC CAG CTG TTT CGC GAA CTC GAG TTC CGC AGC CTG GTT<br>Glu Arg Val Leu Gln Leu Phe Arg Glu Leu Glu Phe Arg Ser Leu Val<br>                275                   280                  285 | 864 |
| CCT CGA CTT CCG CAA CCG CGC CAG CCG GTG CGG AAG ACG GCG GCA CCA<br>Pro Arg Leu Pro Gln Pro Arg Gln Pro Val Arg Lys Thr Ala Ala Pro<br>290                     295                   300 | 912 |
| GCG AGT CAG CGA CGC GCC GTC CTG ACC GAT GCC GAT TTG AGC GAC CTT<br>Ala Ser Gln Arg Arg Ala Val Leu Thr Asp Ala Asp Leu Ser Asp Leu<br>305                     310                   315            320 | 960 |
| GTC CGG GAT TTG GAA ACC TGT CAG GCC TTT GCG CTC GAT GTA GAG ACG<br>Val Arg Asp Leu Glu Thr Cys Gln Ala Phe Ala Leu Asp Val Glu Thr<br>                    325                   330                  335 | 1008 |
| ACA GCT TTG CAT CCC ATG TAC GCC GAC TTC GTG GGC ATC GCG TTG GCG<br>Thr Ala Leu His Pro Met Tyr Ala Asp Phe Val Gly Ile Ala Leu Ala<br>                340                   345                  350 | 1056 |
| ACA GCT CCC GAC CGG AGT TAT TAC GTG CCG CTC GGA CAC ACG ACG GGT<br>Thr Ala Pro Asp Arg Ser Tyr Tyr Val Pro Leu Gly His Thr Thr Gly<br>                    355                   360                  365 | 1104 |
| GAT ACC CAA TTC GAT ATC GAA CAG GTG TTG CAA CGA CTG GCG CCC TTC<br>Asp Thr Gln Phe Asp Ile Glu Gln Val Leu Gln Arg Leu Ala Pro Phe<br>370                     375                   380 | 1152 |
| CTG CGC CAT CCA GAG AAG CAA CGT TAT GCG CAC CAC GGC AAA TAC GAT<br>Leu Arg His Pro Glu Lys Gln Arg Tyr Ala His His Gly Lys Tyr Asp<br>385                     390                   395            400 | 1200 |
| GCC CTG GTC TTG GAA CGT GCC GGT TTT CCC CGA CCA CAC ATC GAC TTC<br>Ala Leu Val Leu Glu Arg Ala Gly Phe Pro Arg Pro His Ile Asp Phe<br>                    405                   410                  415 | 1248 |

-continued

| | |
|---|---|
| GAT ACG ATG ATC GCC GCC TAC CTA CTG GGC GAA AAT GCT GTC GGC CTC<br>Asp Thr Met Ile Ala Ala Tyr Leu Leu Gly Glu Asn Ala Val Gly Leu<br>           420                      425                      430 | 1296 |
| AAA GAA TTG GCA TTC ACG AAG CTC GGG TGG GAG ATG GAG GAA ATC ACC<br>Lys Glu Leu Ala Phe Thr Lys Leu Gly Trp Glu Met Glu Glu Ile Thr<br>                435                     440                   445 | 1344 |
| GAG CTA ATT GGA CGG GGC AAG AAG CAA CTC ACG ATG GAT CGC GCC GAG<br>Glu Leu Ile Gly Arg Gly Lys Lys Gln Leu Thr Met Asp Arg Ala Glu<br>      450                     455                     460 | 1392 |
| ATC GCA CGG GTC ACG CAA TAC GCC TGT GCC GAC GTC GAG GCG ACA TAC<br>Ile Ala Arg Val Thr Gln Tyr Ala Cys Ala Asp Val Glu Ala Thr Tyr<br>465                     470                     475                     480 | 1440 |
| CGG TTA GTC GAG GTA CTT CGT CCA CAA TTC GAA GCC CAC AAT CAA CTC<br>Arg Leu Val Glu Val Leu Arg Pro Gln Phe Glu Ala His Asn Gln Leu<br>                    485                     490                     495 | 1488 |
| CGG CTG TTC ACC GAA ATC GAA CTT CTT TTC ATC GAT GTA CTG ATC GAC<br>Arg Leu Phe Thr Glu Ile Glu Leu Leu Phe Ile Asp Val Leu Ile Asp<br>           500                     505                     510 | 1536 |
| ATG GAA AAG GCG GGA TTC GCG ATC GAT GTG CCG TAC CTC GAA CAG CTC<br>Met Glu Lys Ala Gly Phe Ala Ile Asp Val Pro Tyr Leu Glu Gln Leu<br>                515                     520                   525 | 1584 |
| TCC ATC ATG CTG GAC GGT CAG CTG CAT GCG CTC GAG CGA CGC ATC TAC<br>Ser Ile Met Leu Asp Gly Gln Leu His Ala Leu Glu Arg Arg Ile Tyr<br>530                     535                     540 | 1632 |
| GAA CTG GCT GGG CAT CCC TTC AAC ATC ACT TCG CCA CAA CAG TTG AGC<br>Glu Leu Ala Gly His Pro Phe Asn Ile Thr Ser Pro Gln Gln Leu Ser<br>545                     550                     555                     560 | 1680 |
| ACC CTG CTT TTC GAC GAA CTC GGC CTG CCT CGC GGC AAA CGA ACC AAG<br>Thr Leu Leu Phe Asp Glu Leu Gly Leu Pro Arg Gly Lys Arg Thr Lys<br>                    565                     570                     575 | 1728 |
| ACT GGG TAT TCA GTT TCT CAA GAA GTG CTC GAG AAT CTC CGC GAT ACC<br>Thr Gly Tyr Ser Val Ser Gln Glu Val Leu Glu Asn Leu Arg Asp Thr<br>            580                     585                     590 | 1776 |
| CAC CCC ATC GTC GAG GCG ATT TTG GAA TAC CGG CAA CTC CTC AAA TTG<br>His Pro Ile Val Glu Ala Ile Leu Glu Tyr Arg Gln Leu Leu Lys Leu<br>                595                     600                   605 | 1824 |
| AAG TCG ACG TAC GTC GAT GCC TTA CCG CGG CAA GTC CAT CCC CAA ACC<br>Lys Ser Thr Tyr Val Asp Ala Leu Pro Arg Gln Val His Pro Gln Thr<br>610                     615                     620 | 1872 |
| GGA CGC GTC CAC ACG ATT TTC CAT CAA ACT GTC GCG GCC ACC GGC CGC<br>Gly Arg Val His Thr Ile Phe His Gln Thr Val Ala Ala Thr Gly Arg<br>625                     630                     635                     640 | 1920 |
| TTG AGT TCC TCC GAC CCG AAC CTT CAG AAC ATT CCT GCT CGC GGC GAG<br>Leu Ser Ser Ser Asp Pro Asn Leu Gln Asn Ile Pro Ala Arg Gly Glu<br>                    645                     650                     655 | 1968 |
| CTG GGA CTC GCC GTT CGC CGC GCC TTC ATC GCT GAC AAT CGC CCA GGT<br>Leu Gly Leu Ala Val Arg Arg Ala Phe Ile Ala Asp Asn Arg Pro Gly<br>            660                     665                     670 | 2016 |
| TAT CGA ATC GCC GAT GAA CCG ATC CTG CTT CTT TCA GCT GAC TAC TCG<br>Tyr Arg Ile Ala Asp Glu Pro Ile Leu Leu Leu Ser Ala Asp Tyr Ser<br>                675                     680                     685 | 2064 |
| CAG ATC GAG CTT CGC CTG ATG GCT CAC TTC AGT CAG GAT CCC GCA CTC<br>Gln Ile Glu Leu Arg Leu Met Ala His Phe Ser Gln Asp Pro Ala Leu<br>           690                     695                     700 | 2112 |
| CTG CGT GCC TTC GCT GAA GGC AAG GAC ATT CAC GCG GCT ACC GCG TCT<br>Leu Arg Ala Phe Ala Glu Gly Lys Asp Ile His Ala Ala Thr Ala Ser<br>705                     710                     715                     720 | 2160 |
| GAA GTG TTC GGG GTC CCA CTC GAC GCG GTC ACG CCA GAG ATG CGT CGC<br>Glu Val Phe Gly Val Pro Leu Asp Ala Val Thr Pro Glu Met Arg Arg<br>                    725                     730                     735 | 2208 |

-continued

```
ATC GCG AAA GTC GTC AAT TTC GGC ATC ATG TAT GGG ATG CAA GCG TAC    2256
Ile Ala Lys Val Val Asn Phe Gly Ile Met Tyr Gly Met Gln Ala Tyr
        740                 745                 750

GGC CTC GCT CGC GAC ACC GGT ATG AGC CGT CAA GAC GCA CAG CGC TTC    2304
Gly Leu Ala Arg Asp Thr Gly Met Ser Arg Gln Asp Ala Gln Arg Phe
            755                 760                 765

ATC GAA GCG TAT TTT CAG CGC TTC CCC GGC GTC GCC CGT TAT CTC GAA    2352
Ile Glu Ala Tyr Phe Gln Arg Phe Pro Gly Val Ala Arg Tyr Leu Glu
770                 775                 780

GAA ACG AGA CGC GTG GCG GCC GAA CTC GGT TAC GTC GAA ACG CTC TTC    2400
Glu Thr Arg Arg Arg Ala Ala Glu Leu Gly Tyr Val Glu Thr Leu Phe
785                 790                 795                 800

GGC CGG CGG CGA TAC TTG CCC GAA ATC ACC TCC TCC AAC CCG GCA CGA    2448
Gly Arg Arg Arg Tyr Leu Pro Glu Ile Thr Ser Ser Asn Pro Ala Arg
                805                 810                 815

CGG CAG GCG GCC GAA CGG ATG GCG GTC AAT ATG CCG CTG CAA GGC ACC    2496
Arg Gln Ala Ala Glu Arg Met Ala Val Asn Met Pro Leu Gln Gly Thr
            820                 825                 830

GCA GCC GAT ATT ATG AAG TTG GTC ATG ATC GCT GTC CAC CGA CCG CTG    2544
Ala Ala Asp Ile Met Lys Leu Val Met Ile Ala Val His Arg Pro Leu
835                 840                 845

GGC GAA CGC GGC TTG CGC AGC CGC ATG CTG CTC CAG GTT CAT GAC GAA    2592
Gly Glu Arg Gly Leu Arg Ser Arg Met Leu Leu Gln Val His Asp Glu
850                 855                 860

CTC GTC TTG GAG GTA CCG GAG TCG GAA CTT GCG ACG ACA ACG GAA CTC    2640
Leu Val Leu Glu Val Pro Glu Ser Glu Leu Ala Thr Thr Thr Glu Leu
865                 870                 875                 880

GTC ACG ACA CGC ATG AGT CGC GTC GTC GAA CCC AGC GTG CCA CTC GAA    2688
Val Thr Thr Arg Met Ser Arg Val Val Glu Pro Ser Val Pro Leu Glu
                885                 890                 895

GTC GAT GCC AAA GCG GGG CCC AAT TGG GCT GAC CTT GAG CCG GTT CGA    2736
Val Asp Ala Lys Ala Gly Pro Asn Trp Ala Asp Leu Glu Pro Val Arg
            900                 905                 910

GTG AAA CTC TCC CAC TAG                                            2754
Val Lys Leu Ser His
            915
```

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:2:

TCCGAYCCCA ACCTSCAGAA CATCCC                                       26

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:3:

AGGASSAGCT CGTCGTGSAC CTG                                          23

(2) INFORMATION FOR SEQ ID NO:4:

```
    (i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

CGAACGCGGC TTGCGCAGCC GCAT                                              24

(2) INFORMATION FOR SEQ ID NO:5:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

TGGACAGCGA TCATGGCCAA CTTC                                              24

(2) INFORMATION FOR SEQ ID NO:6:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

ATTGGGCTGA CCTTGAGCCG G                                                 21

(2) INFORMATION FOR SEQ ID NO:7:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

CCCGCTTTGG CATCGACTTC G                                                 21

(2) INFORMATION FOR SEQ ID NO:8:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:8:

GACTACTCGC AGATCGAGCT TCGC                                              24

(2) INFORMATION FOR SEQ ID NO:9:

(i) SEQUENCE CHARACTERISTICS:
         (A) LENGTH: 25 base pairs
         (B) TYPE: nucleic acid
         (C) STRANDEDNESS: single
```

(D) TOPOLOGY: linear (ii) MOLECULE TYPE: cDNA (xi) SEQUENCE DESCRIPTION: SEQ ID NO:9:

GCGATTGCTA GCGATGAAGG CGCGG                                                       25

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GACATGGAAA AGGCGGGATT CGCGATC                                                     27

(2) INFORMATION FOR SEQ ID NO:11:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

TCGATTTCGG TGAACAGCCG GA                                                          22

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

GATGCAAAGC TGTCGTCTCT ACATC                                                       25

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

TGTACCCCGA CTTCGTGGGC ATCG                                                        24

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

```
TCCCGGGAAT CGGCGAGAAG AC                                                    22

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCAGGAATGT TGTCGGACGG                                                       20

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGGGAATTCC ATATGCCGGA GCGCTCACGT CGACCACG                                   38

(2) INFORMATION FOR SEQ ID NO:17:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCCGGAATTC CTAGTGGGAG AGTTTCACTC GAACCGG                                    37

(2) INFORMATION FOR SEQ ID NO:18:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AAGCTTGCAT GCGGAGGTTT AATAATGAAC ACTCAAAAAC CTTTTGAA                        48

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CTAGGATCCT TATATATTAA TTATCCATCT ACAAAGAGA                                  39
```